United States Patent [19]

Kamio et al.

[11] Patent Number: 4,910,128
[45] Date of Patent: Mar. 20, 1990

[54] SILVER HALIDE COLOR PHOTOGRAPHIC MATERIAL

[75] Inventors: Takayoshi Kamio; Katsuyoshi Yamakawa; Hidetoshi Kobayashi; Isamu Itoh, all of Kanagawa, Japan

[73] Assignee: Fuji Photo Film Co., Ltd., Kanagawa, Japan

[21] Appl. No.: 245,941

[22] Filed: Sep. 19, 1988

Related U.S. Application Data

[63] Continuation of Ser. No. 48,360, May 11, 1987, abandoned, which is a continuation of Ser. No. 761,720, Aug. 2, 1985, abandoned.

[30] Foreign Application Priority Data

Aug. 3, 1984 [JP] Japan .................... 59-163545

[51] Int. Cl.⁴ .................... G03C 1/08; G03C 7/34
[52] U.S. Cl. .................... 430/553
[58] Field of Search .................... 430/553

[56] References Cited

U.S. PATENT DOCUMENTS

| | | | |
|---|---|---|---|
| 4,513,079 | 4/1985 | Sakanoue et al. | 430/553 |
| 4,518,680 | 5/1985 | Koboshi et al. | 430/553 |
| 4,525,450 | 6/1985 | Itoh et al. | 430/555 |
| 4,537,856 | 8/1985 | Kurematsu et al. | 430/553 |

FOREIGN PATENT DOCUMENTS

| | | | |
|---|---|---|---|
| 3429257 | 2/1985 | Fed. Rep. of Germany | 430/553 |
| 111643 | 6/1984 | Japan | 430/553 |

Primary Examiner—Paul R. Michl
Assistant Examiner—Janet C. Baxter
Attorney, Agent, or Firm—Sughrue, Mion, Zinn, Macpeak & Seas

[57] ABSTRACT

A silver halide color photographic material comprising as a cyan-dye-forming coupler a compound represented by of formula (I)

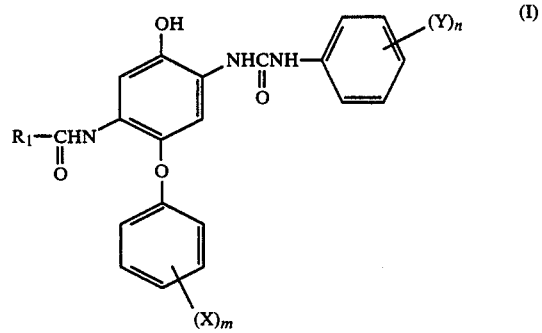

wherein $R_1$ represents a ballast group imparting diffusion fastness to the coupler of formula (I) and a cyan dye formed from said coupler; X represents a hydrogen atom or a group represented by —R, —OR, —SR,

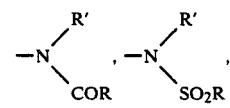

—COR, —COOR, —SO₂R, —SO₂OR,

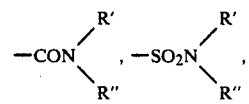

or —OCOR; Y represents a halogen atom, a cyano group, a trifluoromethyl group, a nitro group, or a group represented by —R, —OR, —SR, —COR, —COOR, —SO₂R, —SO₂OR,

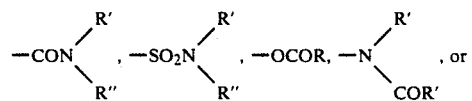

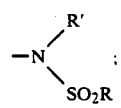

m and n each represents an integer of 1 to 5, and when m or n is more than 1, the X or Y, respectively, are the same or different; R represents an aliphatic group, an aromatic group, or a heterocyclic group, and R' and R" each represents a hydrogen atom, an aliphatic group, an aromatic group, or a heterocyclic group; with the proviso that the total number of carbon atoms in the substituent $(X)_m$ is 4 or more.

11 Claims, No Drawings

SILVER HALIDE COLOR PHOTOGRAPHIC MATERIAL

This is a Continuation of application Ser. No. 07/048,360, filed May 11, 1987, which is a continuation of application Ser. No. 06/761,720 filed August 2, 1985, both now abandoned.

FIELD OF THE INVENTION

This invention relates to cyan-dye-forming couplers (also referred to herein more simply as "cyan couplers"), and more specifically, it relates to silver halide color photographic materials containing novel cyan couplers having a particular aryloxy group at the 4-position removable by coupling with an oxidized form of an aromatic primary amine color developing agent, and other particular substituents at the 2-position and the 5-position.

BACKGROUND OF THE INVENTION

When a conventional silver halide photographic material is exposed to light and subsequently color developed, and aromatic primary amine developer oxidized thereby reacts with a dye forming coupler to form a color image. In general, this method utilizes color reproduction by a subtractive color process, and in order to reproduce blue, greem, and red, color images of yellow, magenta, and cyan, which are in the complementary relationship thereto, respectively, are formed. For forming cyan color images, phenol derivatives or naphthol derivatives are often used as couplers. In color photography, the color forming coupler is either added to a developing solution or included in a photosensitive photographic emulsion layer or other color image forming layer, and by reacting with an oxidized form of a color developer formed by development, a nondiffusing dye is formed.

The reaction of the coupler and the color developer takes place at the active site of the coupler (referred to as the "coupling position"), and a coupler having only hydrogen atoms on this active site is a four-equivalent coupler, i.e., stoichiometrically requiring 4 moles of silver halide having developing nuclei for forming 1 mole of dye. On the other hand, a coupler having a removable group as an anion at the active site is a two-equivalent coupler, i.e., a coupler which stoichiometrically requires only 2 moles of silver halide developing nuclei for forming 1 mole of dye. Therefore, as compared with the 4-equivalent coupler, since the amount of the silver halide in the photosensitive layer may be lowered and hence the thickness thereof may be reduced, it is possible to shorten the time required for processing the photosensitive material, and furthermore, sharpness of the formed color image in enhanced.

Of the phenol type couplers and naphthol type couplers known as cyan color forming couplers, it is disclosed, e.g., in Japanese Patent Application (OPI) Nos. 65134/81, 204,543/82, 204,544/82, 204,545/82, 33249/83, 33250/83 etc. (the term "OPI" as used herein refers to a "published unexamined Japanese patent application"), that phenol type couplers having a phenylureido group at the 2-position and further an acylamino group at the 5-position are superior to the other cyan couplers in light fastness of the color images formed by color development.

However, most of the phenol type two-equivalent couplers having a phenylureido group at the 2-position, an acylamino group at the 5-position and a removable group at the 4-position have some drawbacks. For example, the coupling activity is insufficient, color fogging is easily brought about, dispersibility is poor and coating problems occur, the coupler itself is unstable and cannot stand long-term storage, and so forth.

SUMMARY OF THE INVENTION

Accordingly, one object of this invention is to provide silver halide photographic materials utilizing novel phenolic cyan couplers having excellent heat and light fastness properties in the color developed image and having remarkably improved color developing properties and dispersibility.

Further, another object of this invention is to present couplers with which there is substantially no reduction in the developed color density even when treated with a bleaching solution having a weak oxidizing power or an exhausted bleaching solution.

It has now been found that the above-described objects of this invention are achieved by silver halide color photographic material containing cyan-dye-forming couplers of formula (I)

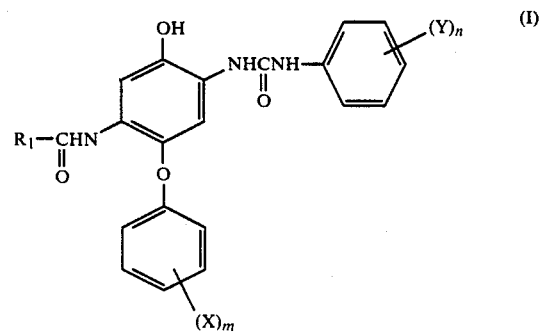

wherein $R_1$ represents a ballast group imparting diffusion fastness to the coupler of formula (I) and a cyan dye formed from said coupler, and preferably represents an aliphatic group, an aromatic group, or a heterocyclic group, each having from 4 to 32 carbon atoms; X represents a hydrogen atom or a gorup represented by —R, —OR, —SR,

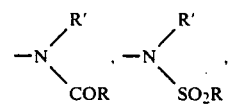

—COR, —COOR, —SO$_2$R, —SO$_2$OR,

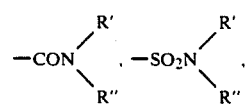

or —OCOR; Y represents a halogen atom, a cyano group, a trifluoromethyl group, a nitro group, or a group represented by —R, —OR, —SR, —COR, —COOR, —SO$_2$R, —SO$_2$OR,

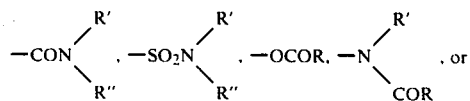

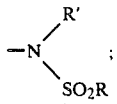

m and n each represents an integer of 1 to 5, and when m or n is more than 1, then X or Y may be the same or different respectively; R represents an aliphatic group, an aromatic group, or a heterocyclic group, and R' and R" each represents a hydrogen atom, an aliphatic group, an aromatic group, or a heterocyclic group; with the proviso that the total number if carbon atoms in the substituent (X) is 4 or more.

As herein used, the aforesaid aliphatic group means a straight-chain or branched-chain alkyl, alkenyl, or a alkynyl group, which may optionally be substituted. The terminology aromatic group means a substituted or unsubstituted aryl group, and the terminology heterocyclic group means a substituted or unsubstituted monocyclic or fused hetero ring.

Preferred substituent in formula (I) are described below. $R_1$ preferably represents a substituted or unsubstituted alkyl or aryl group, and especially preferably a tertiary alkyl group having from 4 to 32 carbon atoms or a group represented by formula (II)

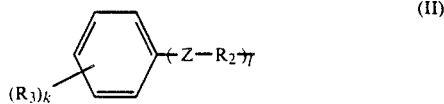

wherein Z represents an oxygen atom, a sulfur atom, —SO—, or —SO$_2$; k represents an integer of 0 to 4, and l represents 0 or 1, and when k is 2 or higher, the $R_3$ are the same or different; $R_2$ represents a straight-chain or branched-chain alkylene group having from 1 to 24 carbon atoms; and $R_3$ represents a monovalent group, for example, a hydrogen atom, a halogen atom (preferably cholorine or bromine), an alkyl group (preferably a straight-chain or branched-chain alkyl group having from 1 to 20 carbon atoms, e.g., methyl, tert-butyl, tert-amyl, tert-octyl, hexadecyl, benzyl, etc.), an aryl group (e.g., phenyl, etc.), a heterocyclic group, an alkoxy group (perferably a straight-chain or branched-chain alkyloxy group having from 1 to 20 carbon atoms, e.g., methoxy, tert-butyloxy, etc.), an aryloxy group (e.g., phenoxy, hydroxyphenylsulfonyl, etc.), a hydroxyl group, an acyloxy group (preferably and alkylcarbonyloxy group or an arylcarbonyloxy group, e.g., acetoxy, benzoyloxy, etc.), a carboxyl group, an alkoxycarbonyl group (preferably a straight-chain or branched-chain alkyloxycarbonyl group), an aryloxycarbonyl group, an alkylthio group, an acyl group (preferably a straight-chain or branched-chain alkylcarbonyl group having from 1 to 20 carbon atoms), a.carbonamido group (preferably a straight-chain or branched-chain alkylcarbonamido group having from 1 to 20 carbon atoms or an arylcarbonamido group), a sulfonamido group, a carbamoyl group, a sulfamoyl group, etc.

X preferably represents a halogen atom or a substituted or unsubstituted alkyl, aryl, alkoxy, alkoxycarbonyl, or carbonamido group; more preferably one of X represents an alkyl or aryl group present at the para-position with respect to the oxygen atom attached to the active site for the coupling reaction. The total number of carbon atoms of the substituent $(X)_m$ is preferably from 4 to 32, and more preferably from 8 to 32. Examples of the alkyl group include methyl, ethyl, isopropyl, tert-butyl, tert-amyl, tert-hexyl, tert-octyl, tert-decyl, tert-pentadecyl, cyclopentyl, cyclohexyl, pentadecyl, allyl, hexadecyl, benzyl, sec-dodecyl, sec-octodecyl, etc. Examples of the aryl group include phenyl, 2-methylphenyl, 4-methoxyphenyl, etc.; examples of the alkoxy group include methoxy, ethoxy, dodecyloxy, methoxyethoxy, etc.; examples of the alkoxycarbonyl group include methoxycarbonyl, dodecyloxycarbony, etc.; and examples of the carbonamido group include acetamido, tetradecanamido, etc.

Of the substituent $(Y)_n$, preferably, one of Y represents a group selected from a cyano group, a trifluoromethyl group, an arylsulfonyl group, an alkylsulfonyl group, a sulfonamido group, a sulfamoyl group, a carbamoyl group, or an alkoxycarbonyl group; more preferably, n=1 and Y represents a cyano group and is present at the para-position with respect to the ureido group. Examples of the arylsulfonyl group include benzenesulfonyl, toluenesulfonyl, etc.; examples of the alkylsulfonyl group include methanesulfony, propanesulfonyl, butanesulfonyl, benzylsulfonyl, tryfluoromethanesulfony, etc.; examples of the sulfonamido group include methanesulfonamido, toluenesulfonamido, triflouromethanesulfonamido, etc.; examples of the sulfamoyl group include sulfamoyl, diethylsulfamoyl, methylsulfamoyl, etc.; examples of the carbamoyl group include carbamoyl, dimethylcarbamoyl, methoxyethylcarbamyl, etc.; and examples of the alkoxycarbonyl group include methoxycarbonyl, ethoxycarbonyl, etc.

The compounds of formula (I) (hereinafter also referred to as "the couplers of this invention") are couplers preferably characterized by having a substituted phenylureido group at the 2-position of the phenol and also a ballasting carbonamido group having from 8 to 32 carbon atoms in total at the 5-position, and further having a substituted phenyloxy group having 4 or more carbon atoms in total in the substituent at the 4-position as a removable group upon formation of a cyan color image by a coupling reaction with a color developer in the oxidized form.

Heretofore, as examples of the phenolic cyan couplers having a substituted phenylureido group at the 2-position, an aryloxy group at the 4-position and a carbonamido group at the 5-position, there have been disclosed, for example, examples of a phenoxy group at the 4-position in Japanese Patent Application (OPI) No. 65134/81, examples of a 3-chlorophenoxy group and a 4-methoxyphenoxy group in the amendment of Japanese Patent Application (OPI) No. 121,330/84, examples of a 3-methylphenoxy group and a 4-methoxyphenyl group at the 4-position in the amendment of Japanese Patent Application (OPI) No. 121,331/84, and examples of a 4-malonamidophenoxy group at the 4-position in Japanese Patent Application (OPI) Nos. 111,643/84 and 111,644/84. However, with these couplers having an aryloxy group having a small number of carbon atoms and hence relatively low lipophilic nature at the 4-position, there are problems such as that the solubility in low boiling organic solvents such as ethyl acetate, etc., and in high boiling organic solvents such as dibutyl phthalate, dioctyl phthalate, trioctyl phosphate, tricresyl phosphate, etc. is poor. Thus, sometimes the emulsion stability is deteriorated or coating problems occur due to crystallization of the coupler, so that even if the solubility is adequate, the color developing properties are low. On the other hand, the couplers of this invention are characterized by having a highly lipophilic aryloxy group having 4 or more carbon atoms in total in the substituent at the 4-position, whereby the objects to be solved by this invention have thus been achieved. That is, they are excellent in solubility in both low boiling and high boiling organic solvents and can prevent coating problems. In addition, since the developed color density and sensitivity are high and the color developing properties are excellent, it is possible to reduce the content of the silver halide. Further, the dyes obtained from the couplers of this invention not only exhibit excellent fastness to light and heat, but also have the feature that there is no substantial reduction in the developed color density even when treated with a bleaching solution having a weak oxidizing power or an exhausted bleaching solution, and therefore they are suitable for rapid processing treatment or treatment not using a coupling accelerator such as benzyl alcohol, etc., as well as for normal processing treatment. These features have been surprising beyond expectation.

Preferred phenolic cyan couplers of this invention are illustrated below, but such should not be considered as limiting this invention.

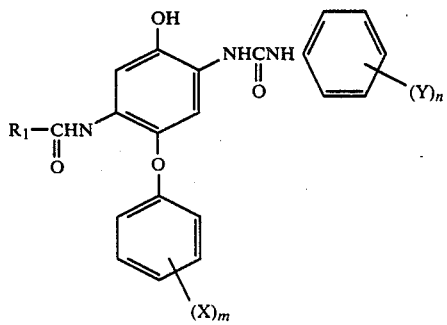

| Compound Example | $R_1$ | X | Y | m | n |
|---|---|---|---|---|---|
| (1) | (t)C$_5$H$_{11}$—⟨ ⟩—OCH(C$_4$H$_9$)CO—, C$_5$H$_{11}$(t) | (t)C$_5$H$_{11}$— (2, 4)* | NC— (4)** | 2 | 1 |
| (2) | (t)C$_5$H$_{11}$—⟨ ⟩—OCH(C$_6$H$_{13}$)CO—, C$_5$H$_{11}$(t) | (t)C$_4$H$_9$— (4) | NC— (4) | 1 | 1 |
| (3) | (t)C$_5$H$_{11}$—⟨ ⟩—OCH(C$_4$H$_9$)CO—, C$_5$H$_{11}$(t) | (t)C$_8$H$_{17}$— (4) | NC— (4) | 1 | 1 |
| (4) | (t)C$_5$H$_{11}$—⟨ ⟩—OCH(C$_2$H$_5$)CO—, C$_5$H$_{11}$(t) | (t)C$_8$H$_{17}$— (2, 4) | NC— (4) | 2 | 1 |
| (5) | (t)C$_8$H$_{17}$—⟨ ⟩—OCH(C$_6$H$_{13}$)CO—, C$_8$H$_{17}$(t) | (t)C$_8$H$_{17}$— (4) | Cl— (3, 4) | 1 | 2 |
| (6) | (t)C$_5$H$_{11}$—⟨ ⟩—OCH(C$_2$H$_5$)CO—, C$_5$H$_{11}$(t) | (t)C$_8$H$_{17}$— (4) | C$_4$H$_9$SO$_2$— (4) | 1 | 1 |

-continued

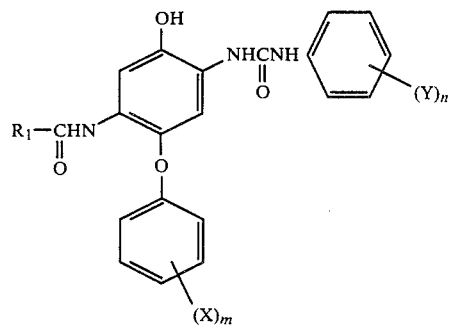

| Compound Example | R₁ | X | Y | m | n |
|---|---|---|---|---|---|
| (7) | (t)C₅H₁₁—⌬(C₅H₁₁(t))—OCHCO— (C₄H₉) | (t)C₅H₁₁— (4) | CH₃SO₂— (4) | 1 | 1 |
| (8) | (t)C₅H₁₁—⌬(Cl)—OCHCO— (C₆H₁₃) | n-C₁₅H₃₁— (3) | NC— (4) | 1 | 1 |
| (9) | (t)C₅H₁₁—⌬(C₅H₁₁(t))—OCHCO— (C₄H₉) | n-C₈H₁₇O— (4) | CH₃SO₂NH— (3) | 1 | 1 |
| (10) | (t)C₅H₁₁—⌬(C₅H₁₁(t))—OCHCO— (C₂H₅) | CH₃—, n-C₁₀H₂₁— (4)    (2) | —SO₂N(C₂H₅)₂ | 2 | 1 |
| (11) | (t)C₅H₁₁—⌬(C₅H₁₁(t))—OCHCO— (C₂H₅) | (t)C₈H₁₇—, CH₃O— (4)    (2) | CF₃— (4) | 2 | 1 |
| (12) | (t)C₅H₁₁—⌬(C₅H₁₁(t))—SCHCO— (C₂H₅) | (t)C₈H₁₇— (4) | C₄H₉SO₂— (4) | 1 | 1 |
| (13) | (t)C₅H₁₁—⌬(C₅H₁₁(t))—OCHCO— (C₆H₁₃) | (t)C₈H₁₇—, CH₃CONH— (4)    (2) | NC— (4) | 2 | 1 |
| (14) | (t)C₅H₁₁—⌬(C₅H₁₁(t))—OCHCO— (C₄H₉) | (t)C₁₀H₂₁—, Cl— (4)    (2) | NC— (4) | 2 | 1 |

-continued

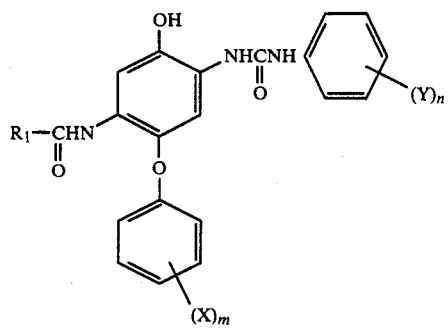

| Compound Example | R₁ | X | Y | m | n |
|---|---|---|---|---|---|
| (15) | (t)C₅H₁₁—⟨benzene with C₅H₁₁(t)⟩—OCH(C₄H₉)CO— | (t)C₈H₁₇— (4) | Cl—, NC— (2)  (4) | 1 | 2 |
| (16) | ⟨benzene with Cl⟩—OCH₂C(CH₃)₂—CO— | (t)C₁₀H₂₁— (4) | NC— (4) | 1 | 1 |
| (17) | HO—⟨C₆H₄⟩—SO₂—⟨C₆H₄⟩—OCH(C₁₂H₂₅)CO— | (t)C₈H₁₇— (4) | NC— (4) | 1 | 1 |
| (18) | CH₃—⟨benzene with C₁₀H₂₁-n⟩—OCH(C₆H₁₃)CO— | (t)C₅H₁₁— (2, 4) | NC— (4) | 2 | 1 |
| (19) | CH₃—⟨benzene with C₈H₁₇(t)⟩—OCH(C₄H₉)CO— | (t)C₈H₁₇— (4) | C₂H₅OCO— (4) | 1 | 1 |
| (20) | CH₃—⟨benzene with C₈H₁₇(t)⟩—OCH(C₄H₉)CO— | (t)C₈H₁₇— (4) | NC— (4) | 1 | 1 |

*Indicates the position of substituent X relative to the oxygen atom of the phenoxy group.
**Indicates the position of substituent Y relative to the ureido group of the phenylureido group.

The cyan dye forming couplers of this invention may be easily synthesized according to the following general synthetic process.

Scheme I

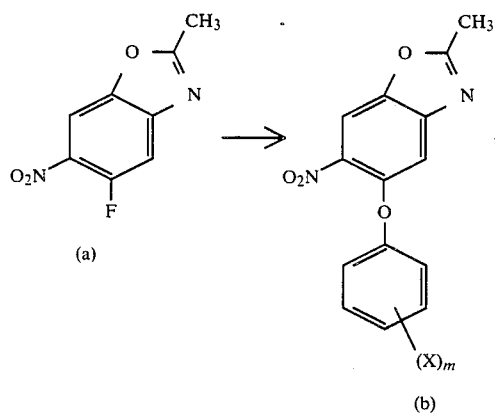

(a) → (b)

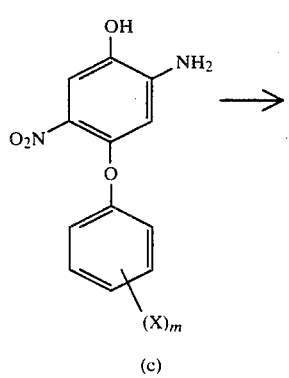

(c) →

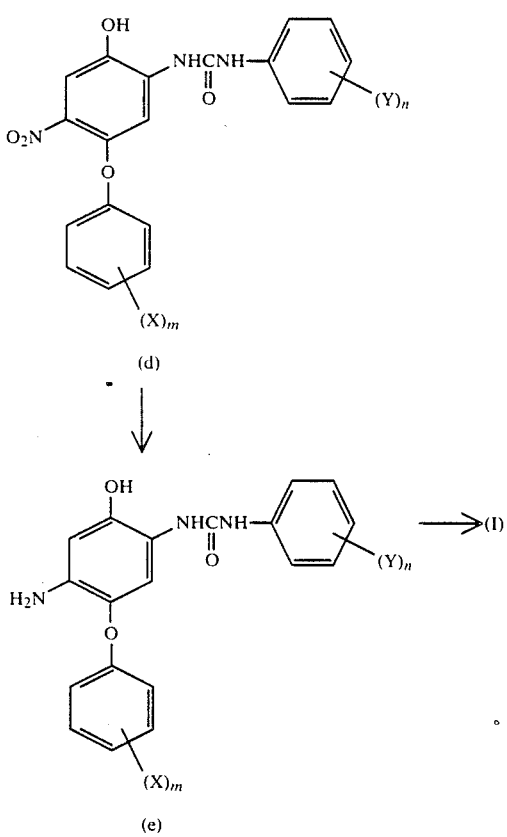

(d)

↓

(e) → (I)

In Scheme I, $R_1$, X, Y, m and n are as defined above for formula (I). A specific synthesis example is given below.

SYNTHESIS EXAMPLE

Synthesis of Coupler (1)

Synthesis of 2-Methyl-5-(2,4-di-tert-amylphenoxy)-6-nitrobenzoxazole (1b)

To an ice-cooled solution of 117.0 g of 2,4-tert-amylphenol in 500 ml of tetrahydrofuran was added 20 g of 60% sodium hydride, and stirred for 15 minutes. A solution of 5-fluoro-2-methyl-6-nitrobenzoxazole (1a) in 300 ml of tetrahydrofuran was added thereto and reacted at 40° C. for 6 hours. The tetrahydrofuran was distilled off under reduced pressure, the residue was crystallized with methanol-water to obtain 145 g of 2-methyl-5-(2,4-di-tert-amylphenoxy)-6-nitrobenzoxazole (1b).

Synthesis of 2-Amino-4-(2,4-di-tert-amylphenoxy)-6-nitrophenol (1c)

A mixture of 145 g of (1b), 200 ml of conc. hydrochloric acid and 700 ml of ethanol was reacted at 70° C. for 5 hours, then poured into water, extracted with ethyl acetate, washed with water, and the solvent was distilled off under reduced pressure. The residue was crystallized with n-hexane to obtain 115 g of (1c). m.p. 144°–148° C.

Synthesis of 2-[3-(4-Cyanophenyl)ureido]-4-(2,4-di-tert-amylphenoxy)-5-nitrophenol (1d)

A mixture of 39 g of (1c), 24 g of phenyl p-cyanophenyl carbamate, 0.5 g of imidazole and 80 ml of acetonitrile was heated at reflux for 10 hours. After completion of the reaction, the reaction mixture was allowed to stand at room temperature (about 20° C.), and the separated crystals were filtered off to obtain 34 g of (1d). m.p. 212°–215° C.

Synthesis of Coupler (1)

27 g of (1d) and 1 of a palladium-carbon catalyst were added to 100 ml of dimethylacetamide, and catalytic reduction was effected in an autoclave. After the theoretical amount of hydrogen had been consumed, the catalyst was filtered out, 19.2 g of 2-(2,4-di-tert-amylphenoxy)hexanoly chloride was added to the filtrate and stirred in a nitrogen atmosphere at 60° C. for 2 hours. The reaction mixture was poured into water, extracted with ethyl acetate, washed with water, and concentrated under reduced pressure. The resulting oil was crystallized with n-hexane/ethyl acetate to obtain 29 g of exemplified Coupler (1). m.p. 208°–210° C.

Other couplers were also synthesized by similar procedures.

The amount of the couplers of this invention added is generally from $1 \times 10^{-3}$ mole to $7 \times 10^{-1}$ mole, and preferably from $1 \times 10^{-2}$ mole to $5 \times 10^{-1}$ mole, per mole of silver in a silver halide emulsion layer constituting a photosensitive layer of the material.

The couplers of this inventions and couplers used in combination with this invention described hereinafter may be incorporated into photosensitive materials by various known dispersing methods, and representative examples thereof include a solid dispersing method, and alkali dispersing method, preferably a latex dispersing method, more preferably an oil-in-water dispersing method, etc. In the oil-in-water dispersing method, the coupler may be dissolved in either a single solvent or a mixed solvent of a high boiling organic solvent having a boiling point of 175° C. or higher and a low boiling solvent, i.e., a so-called co-solvent, and finely dispersed in water or an aqueous solvent such as a gelatin aqueous solution in the presence of a surfactant. Examples of the high boiling organic solvents are described in U.S. Pat. No. 2,322,027, etc. Dispersing may be accompanied by phase inversion, and, if needed, the co-solvent may be removed or reduced by distillation, noodle washing with water, ultrafiltration, etc., before use in coating.

Specific examples of the high boiling organic solvent include phathalic acid esters (dibutyl phthalate, dicyclohexyl phthalate, di-2-ethylhexyl phthalate, didodecyl phthalate, etc.) esters of phosphoric acid or phosphonic acid (triphenyl phosphate, tricresyl phosphate, 2-ethylhexyl-diphenyl phosphate, tri-2-ethylhexyl phosphate, tridecyl phosphate, tributoxyethyl phosphate, trichloropropyl phosphate, di-2-ethylhexyl-phenyl phosphonate, etc.), benzoic acid esters (2-ethylhexyl benzoate, dodecyl benzoate, 2-ethylhexyl p-hydroxybenzoate, etc.), amides (diethyldodecanamide, N-tetradecylpyrrolidone, etc.), alcohols or phenols (isostearyl alcohol, 2,4-di-tert-amylphenol, etc.), aliphatic carboxylic acid esters (dioctyl azelate, glycerol tributyrate, isostearyl lactate, triotyl citrate, etc.), aniline derivatives (N,N-dibutyl-2-butoxy-5-tert-octylaniline, etc.), hydrocarbons (paraffin, dodecylbenzene, diisopropylnaphthalene, etc.), etc. As the co-solvent, an organic solvent having a boiling point of from about 30° to 160° C. may be used, and representative examples thereof include ethyl acetate, butyl acetate, ethyl propionate, methyl ethyl ketone, cyclohexanone, 2-ethoxyethyl acetate, dimethylformamide, etc.

Specific examples of the process steps and effects of the latex dispersing method and impregnating latexes are described in U.S. Pat. No. 4,199,363, German offenlegungschrift (OLS) 2,541,271, German OLS No. 2,541,230, etc.

Various color couplers may be used in this invention. As used herein, color couplers means compounds capable of forming dyes by reacting an oxidized form of an aromatic primary amine developing agent. Representative examples of useful color couplers include naphthol or phenol type compounds, pyrazolone or pyrazoloazole type compounds and open ring or heterocyclic ketomethylene compounds. Specific examples of the cyan, magenta and yellow couplers which may be used in this invention are described in the patent cited in Research Disclosure, RD Nos. 17643 (Dec., 1978) VII-D and 18717 (Nov., 1979).

These couplers preferably have a ballast group or have been polymerized, and hence are nondiffusing, The coupling position is preferably substituted by a removable group rather than a hydrogen atom. It is also possible to use a coupler imparting appropriate diffusing properties to the resulting developed dye, a colored coupler, a colorless coupler, or a coupler releasing a development retarder or a development accelerator upon the coupling reaction.

As the yellow couplers which may be used in this invention, oil protected type acylacetamide type couplers may be mentioned as representative examples. Specific examples thereof are described in U.S. Pat. Nos. 2,407,210, 2,875,057, 3,265,506, etc. Two equivalent yellow couplers may preferably be used in this invention, and representative examples thereof are oxygen atom removing type yellow couplers as described in U.S. Pat. Nos. 3,408,194, 3,447,928, 3,933,501, 4,401,752, etc., or nitrogen atom removing type yellow couplers as described in Japanese Patent Publication No. 10739/83, U.S. Pat. Nos. 4,022,620, 4,326,024, Research Disclosure, RD No. 18053 (April, 1979), British Pat. No. 1,425,020, German OLS Nos. 2,219,917, 2,261,361, 2,329,587, 2,433,812, etc. α-Pivaloylacetanilide type couplers are characterized by fastness of the developed dye, while α-benzoylacetonitrile type couplers are characterized by good color developing properties.

As the magenta couplers which may be used in this invention, there may be mentioned couplers of oil protected type indazolone or cyanoacetyl type, preferably 5-pyrazolone type and pyrazoloazole type such as pyrazolotriazoles, etc. Of the 5-pyrazolone type couplers, those having an arylamino group or an acylamino group substituted at the 3-position are preferred from viewpoints of the hue of the developed dye and the developing speed. Representative examples thereof are described in U.S. Pat. Nos. 2,311,082, 2,343,703, 2,600,788, 2,908,573, 3,062,653, 3,152,896, 3,936,015, etc. Two-equivalent 5-pyrazolone type couplers are preferred, and as the leaving group, a nitrogen atom leaving group as described in U.S. Pat. No. 4,310,619 or an arylthio group as described in U.S. Pat. No. 4,351,897 is preferred. 5-Pyrazolone type couplers having a ballast group as described in European Pat. No. 73,636 have high color developing reactivity.

Examples of the pyrazoloazole type couplers include pyrazolobenzimidazoles described in U.S. Pat. No. 3,369,897, preferably pyrazolo[5,1-c][1,2,4]triazoles as described in U.S. Pat. No. 3,725,067, pyrazolotetrazoles as described in Research Disclosure, RD No. 24220 (June, 1984), and pyrazolopyrazoles as described in Research Disclosure, RD No. 24230 (June, 1984). Imidazopyrazoles described in Japanese Patent Application No. 23434/83 and pyrazolo[1,5-b][1,2,4]triazoles described in Japanese Patent Application No. 45512/83 are most preferred in view of low yellow secondary absorption of the developed dye and light fastness.

As the cyan couplers which may be used in combination with the couplers of this invention, there may be mentioned oil protected type naphthol type and phenol type couplers, and representative examples thereof include naphthol type couplers as described in U.S. Pat. No. 2,474,293, preferably oxygen atom removing type high active two equivalent naphthol type couplers described in U.S. Pat. Nos. 4,052,212, 4,146,396, 4,228,233, and 4,296,200. Specific examples of the phenol type couplers are described in U.S. Pat. Nos. 2,369,929, 2,423,730, 2,772,162, 2,895,826, etc.

Cyan couplers fast (i.e., resistant to heat, moisture, and temperature are preferably used in this invention, and typical examples thereof include phenol type cyan couplers as described in U.S. Pat. No. 3,772,002, 2,5-diacylamino substituted phenol type couplers as described in U.S. Pat. Nos. 2,772,162, 3,758,308, 4,126,396, 4,334,011, 4,327,173, German OLS No. 3,329,729, Japanese Patent Application No. 42671/83, etc., phenol type couplers having a phenylureido group at the 2-position and an acylamino group at the 5-position, as described in U.S. Pat. Nos. 3,446,622, 4,333,999, 4,451,559, 4,427,767, etc., and the like.

The above-described couplers may be used, in order to satisfy the characteristics required of the photosensitive materials, in such a way that two or more thereof are incorporated in the same layer, or that the same compound is added to two or more different layers.

In order to correct unnecessary absorption in a short wavelength region due to the developed dyes of the magenta and cyan couplers, it is preferred to use a colored coupler in combination in color photosensitive materials for photography. Representative examples thereof include yellow-colored magenta couplers as described in U.S. Pat. No. 4,163,670, Japanese Patent Publication No. 39413/82, etc., magenta-colored cyan couplers as described in U.S. Pat. Nos. 4,004,929, 4,138,258, British Pat. No. 1,146,368, etc.

A black-dye-forming coupler used, e.g., for saving silver in photosensitive materials for X-rays may also be used in this invention. Specific examples thereof are described in U.S. Pat. No. 4,126,461, British Pat. No. 2,102,136, etc.

These color couplers may form polymers, i.e., dimers or higher polymers. Representative examples of polymerized couplers are described in U.S. Pat. Nos. 3,451,820 and 4,080,211. Specific examples of polymerized magenta couplers are described in British Pat. No. 2,102,173 and U.S. Pat. No. 4,367,282.

Further, it is possible to improve graininess (i.e., to decrease graininess) by using in combination a developed dye diffusing coupler. Examples of such a coupler may be found, e.g., in the magenta couplers described in U.S. Pat. No. 4,336,237 and British Pat. No. 2,125,570, and specific examples of the yellow, magenta, and cyan couplers are described in European Pat. No. 96,873 and German OLS No. 3,324,533.

This invention may be used in general silver halide color photosensitive materials, such as color negative films, color paper, color positive films, color reversal films for slides, color reversal films for motion pictures, color reversal films for TV, etc. Especially, they are suitably applied to color negative films and various color reversal films for which high sensitivity and high image quality are required. Further, they may also be used in color paper.

The silver halide color photosensitive materials of this invention preferably utilize a UV absorber for enhancing light fastness. Where the UV absorber is incorporated in a protective layer, another protective layer may be coated as the outermost layer. This protective layer may contain a matting agent having particles (diameter not limited), etc.

The aforesaid UV absorber, like the coupler, may be dissolved in either a single solvent or a mixed solvent of a high boiling organic solvent and a low boiling organic solvent and dispersed in a hydrophilic colloid. While the amount of the high boiling organic solvent and the UV absorber is not particularly restricted, it is generally suitable to use the high boiling organic solvent in the range of from 0 to 300% based on the weight of the UV absorber. Compounds which are liquid at normal temperature are preferably used, either alone or in combination.

The use of the aforesaid benzotraizole type UV absorber in combination with the combination of the couplers of this invention improves storability, especially light fastness, of developed dye images, especially cyan images. This UV absorber and the cyan coupler may be co-emulsified.

In order to improve the storability of the developed dye images, especially yellow and magenta images, various organic or metal complex type discoloration inhibitors may be used therewith. Examples of the organic discoloration inhibitors include hydroquinones, gallic acid derivatives, p-alkoxyphenols, p-oxyphenols, etc., and for dye image stabilizers, stain inhibitors or antioxidants, patents are cited in *Research Disclosure*, RD No. 17643, VII, Section I or J. Metal complex type discoloration inhibitors are described in *Research Disclosure*, Rd No. 15162, etc.

In order to improve the heat and light fastness of the yellow images, it is possible to use phenols, hydroquinones, hydroxycoumarones, hydroxycoumarans, hindered amines, and their alkyl ethers, silyl ethers and many compounds belonging to hydrolytic precursor derivatives thereof.

In the silver halide emulsion layer of the color photographic materials of this invention, various silver halides may be used, e.g., silver chloride, silver bromide, silver chlorobromide, silver iodobromide, silver chloroiodobromide, etc. Silver iodobromide containing from 2 to 20 mole % silver iodide and silver chlorobromide containing from 10 to 15 mole % of silver bromide are preferred. There is not restriction on the crystal form, crystal structure, grain diameter, grain diameter distribution, etc., of the silver halide grains. The crystals of the silver halide may be normal or twin, and may be in the form of hexahedron, octahedron, or tetradecahedron. Flat grains of a thickness of not greater than 0.5 microns, a diameter of at least 0.6 microns and an average aspect ratio of 5 or more, as disclosed in *Research Disclosure*, RD No. 22534, may also be used.

The crystal structure may be uniform or of different compositions between the inside and outside, or may be in a stratified structure, of may be of epitaxially joined silver halides having different compositions, or may be composed of a mixture of grains of various crystal forms. Further, they may be either that forming the latent image mainly on the grain surface or that forming it inside.

The grain diameter of the silver halide may be as small as 0.1 micron or less, or as large as 3 mircons, based on the projected area diameter, and its emulsion may be either a single dispersed emulsion having narrow distribution or a multi-dispersed emulsion having large distribution.

These silver halide grains may be produced by known processes conventionally employed in the art.

The above-described silver halide emulsions may be sensitized by conventional chemical sensitization, i.e., sulfur sensitization, noble metal sensitization, or a combination thereof. Further, the silver halide emulsions of this invention may be imparted with color sensitivity to a desired photosensitive wavelength region by using a sensitizing dye. Examples of the dye advantageously used in this invention include methine dyes and styryl dyes as cyanine, hemicyanine, rhodacyanine, merocyanine, oxonol, hemioxonol, etc., and they must be used either singly or in combinations of two or more thereof.

As the base used in this invention, either a transparent base of, e.g., polyethylene terephthalate, cellulose triacetate, etc., or a reflecting base described hereinlater may be used. The reflecting base is preferred, and examples include baryta paper, polyethylene-coated paper, polypropylene type synthetic paper, a transparent base either provided with a reflecting layer or using in combination a reflecting body, for example, glass plates, polyester films of, e.g., polyethylene terephthalate, cellulose triacetate, cellulose nitrate, etc., polyamide films, polycarbonate films, polystyrene films, etc. These bases may be appropriately chosen according to the intended purpose.

The blue-sensitive, green-sensitive, and red-sensitive emulsions are those spectrally sensitized by methine dyes to render color sensitivity, respectively. Examples of the dye used include cyanine dyes, merocyanine dyes, compound cyanine dyes, compound merocyanine dyes, holopolar cyanine dyes, hemicyanine dyes, styryl dyes, and hemioxonol dyes. Particularly useful dyes are cyanine dyes, merocyanine dyes, and compound merocyanine dyes.

The color photographic material of this invention may incorporate, in addition to the above-described constituting layers, auxiliary layers such as a subbing layer, an intermediate layer, a protective layer, etc. Further, as needed, a second UV absorbing layer may be provided between the red-sensitive silver halide emulsion layer and the green-sensitive silver halide emulsion layer. In this UV absorbing layer, although it is preferred to use the above-described UV absorbers, other known UV absorbers may also be used.

While gelatin is advantageous as the binder or the protective colloid for the photographic emulsion, other hydrophillic colloids may also be used.

For example, proteins may be used, such as gelatin derivatives, graft polymers of gelatin and other polymers, albumin, casein, etc.; cellulose derivatives such as hydroxyethyl cellulose, carboxymethyl cellulose, cellulose sulfate esters, etc., sugar derivatives such as sodium alginate, starch derivatives; and various hydrophilic polymeric substances such as homopolymers and copolymers, e.g., polyvinyl alcohol, polyvinyl alcohol partial acetal, poly-N-vinylpyrrolidone, polyacrylic acid, polymethacrylic acid, polyacrylamide, polyvinylimidazole, polyvinylpyrazole, etc.

Gelatins that may be used include lime-treated gelatin, acid-treated gelatin, or enzyme-treated gelatin as described in *Bull. Soc. Sci. Phot. Japan*, No. 16, p. 30 (1966), and further a hydrolysate or enzymatic hydrolysate of gelatin may also be used.

In the photosensitive materials of this invention, the hydrophilic colloid layers of the photographic emulsion layers, etc., may further contain brigthening agents of stilbene type, triazine type, oxazole type, coumarine type, etc. They may be water-soluble, or may be water-insoluble and used in the form of a dispersion. Specific examples of fluorescent brighteners are described in U.S. Pat. Nos. 2,632,701, 3,269,840 and 3,359,102, British Pat. Nos. 852,075 and 1,319,763, description under "Brighteners" of p. 24, left column, lines 9 to 36 of *Research Disclosure*, Vol. 176, RD No. 17643 (published in December, 1978), etc.

In the photosensitive materials of this invention, where dyestuffs, UV absorbers, etc., are contained in the hydrophilic colloid layers, they may also be mordanted by a cationic polymer, etc. For example, polymers described in British Pat. No. 685,475, U.S. Pat. Nos. 2,675,316, 2,839,401, 2,882,156, 3,048,487, 3,184,309 and 3,445,231, German OLS No. 1,914,362, Japanese Patent Application (OPI) Nos. 47642/75, 71332/75, etc. may be used.

The photosensitive materials of this invention may contain, as a fogging inhibitor, hydroquinone derivatives, aminophenyl derivatives, gallic acid derivatives, ascorbic acid derivatives, etc., and specific examples thereof are described in U.S. Pat. Nos. 2,360,290, 2,336,327, 2,403,721, 2,418,613, 2,675,314, 2,701,197, 2,704,713, 2,728,659, 2,732,300 and 2,735,765, Japanese Patent Application (OPI) Nos. 92988/75, 92989/75, 93928/75, 110,337/75, 146,235/77, Japanese Patent Publication No. 23813/75, etc.

The color photographic material of this invention may contain, in addition to those described above, various photographic additives known in this art, for example, stabilizers, fogging inhibitors, surfactants, couplers other than those of this invention, filter dyestuffs, irradiation-preventing dyestuffs, developing agents, etc., as needed, and examples thereof are described in *Research Disclosure*, RD No. 17643, supra.

Further, in some cases, it is also possible to add a finely divided silver halide emulsion substantially free from photosensitivity (e.g., silver chloride, silver bromide, silver chlorobromide emulsions, etc. having an average grain size of $0.20\mu$ or less) to the silver halide emulsion layers and other hydrophilic colloid layers.

The color developing solution which may be used in this invention is preferably an alkaline aqueous solution containing an aromatic primary amine type color developing agent as an active ingredient. Representative examples of the color developing agent include 4-amino-N,N-diethylaniline, 3-methyl-4-amino-N,N-diethylaniline, 4-amino-N-ethyl-N-$\beta$-hydroxyethylaniline, 3-methyl-4-amino-4-ethyl-$\beta$-hydroxyethylaniline, 3-methyl-4-amino-N-ethyl-N-$\beta$-methanesulfonamidoethylaniline, 4-amino-3-methyl-N-ethyl-N-$\beta$-methoxyethylaniline, etc.

The color developing solution may contain pH buffers such as sulfites, borates, phosphates, etc., of alkali metals, development retarders or fogging inhibitors such as bromide, iodide, or organic fogging inhibitors, etc. In addition, it may further contain, as needed, hard water softeners, preservatives such as hydroxylamine, organic solvents such as benzyl alcohol, diethylene glycol, etc., developing accelerators such as polyethylene glycol, quaternary ammonium salts, amines, etc., dye forming couplers, competing couplers, fogging agents such as sodium boron hydride, etc., auxiliary developers such as 1-phenyl-3-pyrazolidone, thickeners, polycarboxylic acid type chelating agents described in U.S. Pat. No. 4,083,723, antioxidants described in German OLS No. 2,662,950, etc.

The photographic emulsion layers of the color developing solution are usually bleached. The bleaching process may be conducted simultaneously with the fixing process or may be conducted separately. As the bleaching agent, compounds of polyvalent metals such as iron (III), cobalt (III), chromium (VI), copper (II), etc., peroxo acids, quinones, nitroso compounds, etc. may be used. Examples of the bleaching agent which may be used include ferricyanide compounds, bichromates, organic complexes of iron (III) or cobalt (III); aminopolycarboxylic acids such as ethylenediaminetetraacetic acid, nitrilotriacetic acid, 1,3-diamino-2-propanoltetraacetic acid, etc.; complexes of organic acids such as citric acid, tartaric acid, malic acid, etc.; persulfates; permanganates; nitrosophenol; etc. Of these, potassium ferricyanide, sodium iron (III) ethylenediaminetetraacetate and ammonium iron (III) ethylenediaminetetraacetate are particularly useful. The iron (III) ethylenediaminetetraacetate complexes are useful in both separate bleaching bath and combined bleaching and fixing bath.

The color development or the bleaching and fixing process may optionally be followed by washing with water. The color development is generally effected at a temperature of from 18° to 55° C., preferably at 30° C.

or higher, and particularly preferably at 35° C. or higher. The time required for the development is in the range of from about 3.5 minutes to about one minute, the shorter time being preferred. The solution is preferably replenished in the case of continuous processing, and a replenisher is supplied in an amount not greater than 330 cc, and preferably not greater than 100 cc, per square meter of the area to be processed. The benzyl alcohol content in the developing solution is preferably not greater than 5 ml/l.

The bleaching and fixing may be conducted at a temperature of from 18° to 55° C., and preferably at 30° C. or higher. By using 35° C. or higher, the processing time may be reduced to one minute or less and the amount of the replenisher may be reduced. The time required for washing after the color development or the bleaching and fixing is generally within 3 minutes. Alternatively, it is possible to use a stabilizing bath substantially without washing.

Developed dyes are deteriorated not only by light and heat, but also are deteriorated and discolored by mildew during storage. Especially, cyan color images are remarkably susceptible to mildew and thus it is preferred to use a mildewproofing agent. Specific examples of mildewproofing agents include 2-thiazolylbenzimidazoles as described in Japanese Patent Application (OPI) No. 157,244/82. The mildewproofing agent may be either incorporated in the photosensitive material, or added from outside in the developing step, or if present in a photographic material of a processing agent, it may be added at any desired step.

This invention is more particularly described by the following examples, but this invention is not restricted by the following examples.

REFERENCE EXAMPLE 1

A solution obtained by adding 20 ml of dibutyl phthalate and 50 ml of ethyl acetate to 20 g of the coupler (1) of this invention and heating at 70° C. was added to 300 ml of an aqueous solution containing 50 g of gelatin and 2.0 g of sodium dodecylbenzenesulfonate, and thereafter passed through a preheated colloid mill five times. The obtained emulsified dispersion was coated on a glass plate to obtain a sample 101. Similarly, samples 102, 103, 104, 105, and 106 were prepared from the couplers of this invention (3) and (20), and the following couplers C-1, C-2, and C-3, respectively.

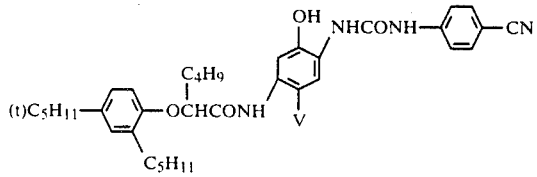

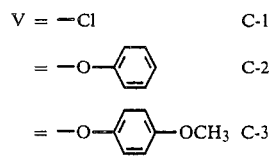

The samples 101–106 were left in a refrigerater at ca. 5° C. for 2 weeks, and thereafter the coated layer conditions were examined. With the samples 104, 105, and 106, the separation of the couplers were obvious to the naked eyes, whereas the samples 101, 102, and 103 in which the couplers of this invention had been dispersed showed no separation of the couplers even by microscopic observation. Thus, it is evident that the couplers of this invention are excellent in solubility in organic solvents and excellent in stability on emulsifying and dispersing.

EXAMPLE 1

A film sample was prepared, which was composed of the respective layers of the following compositions on a cellulose triacetate film base.

| First Layer: Red-sensitive Emulsion Layer | |
|---|---|
| Silver iodobromide emulsion (silver iodide: 5 mole %, ave. grain diameter: 0.4 μ) | |
| Silver dosage | 1.79 g/m² |
| Sensitizing Dye I (per mole of silver) | 6 × 10⁻⁵ mole |
| Sensitizing Dye II (per mole of silver) | 1.5 × 10⁻⁵ mole |
| Coupler EX-1 (per mole of silver) | 0.04 mole |
| Coupler EX-2 (per mole of silver) | 0.003 mole |
| Coupler EX-3 (per mole of silver) | 0.0006 mole |
| Tricresyl phosphate (per mole of the coupler) | 0.5 g |
| Dibutyl phthalate (per mole of the coupler) | 0.5 g |
| Second Layer: Protective Layer | |
| Gelatin layer containing polymethyl methacrylate particles (diameter: ca. 1.5 μm) | |

In addition to the aforesaid composition, 1,3-divinylsulfonyl-2-propanol as a hardener and a surfactant were added to the respective layers. The thus prepared sample was designated as sample 201.

Samples 202, 203, 204, 205, 206, 207 and 208 were prepared by the procedures similar to those for the sample 201, except that the coupler EX-1 in the first layer of the sample 201 was replaced by the equivalent molar amount of the couplers C-4, C-5, C-6, and the couplers of this invention (1), (2), (3) and (6), respectively.

| Compounds used in the samples: | |
|---|---|
| Sensitizing dye I: | Anhydro-5,5'-dichloro-3,3'-di-(γ-sulfopropyl)-9-ethyl-thiacarbocyanine hydroxide pyridinium salt |
| Sensitizing dye II: | Anhydro-9-ethyl-3,3'-di-(γ-sulfopropyl)-4,5,4',5'-dibenzothiacarbocyanine hydroxide triethylamine salt |

-continued
Compounds used in the samples:
EX-1
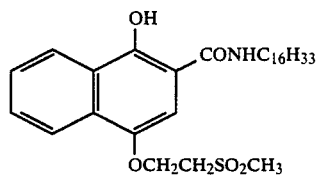
EX-2
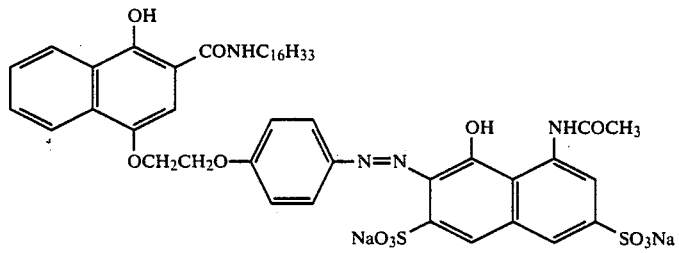
EX-3
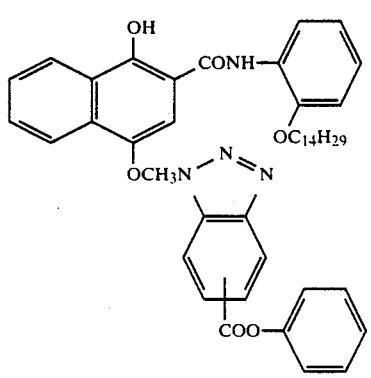
C-4
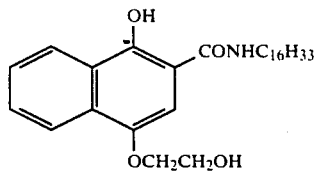
C-5
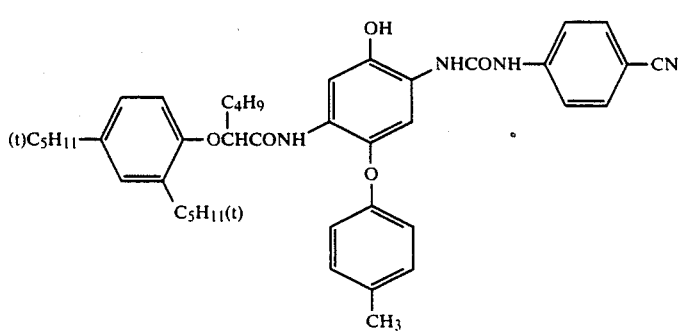

-continued

Compounds used in the samples:

C-6
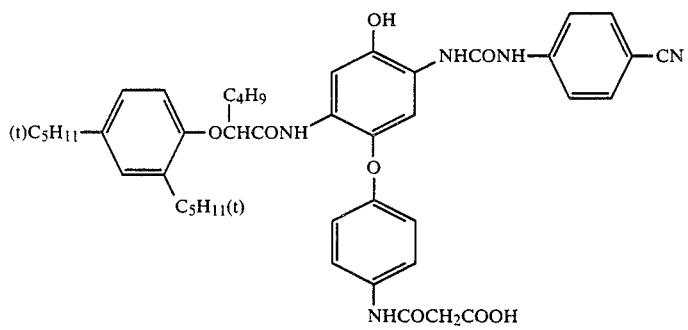

The samples 201–208 obtained were exposed to light for sensitometry, and thereafter developed and processed using the following conditions at 38° C.

| 1. Color development | 3 min. 15 sec. |
| --- | --- |
| 2. Bleaching | 6 min. 30 sec. |
| 3. Washing | 3 min. 15 sec. |
| 4. Fixing | 6 min. 30 sec. |
| 5. Washing | 3 min. 15 sec. |
| 6. Stabilization | 3 min. 15 sec. |

The processing solution compositions used in the respective steps were as follows:

| Color Developing Solution | |
| --- | --- |
| Sodium nitrilotriacetate | 1.0 g |
| Sodium nitrite | 4.0 g |
| Sodium carbonate | 30.0 g |
| Potassium bromide | 1.4 g |
| Hydroxylamine sulfate | 2.4 g |
| 4-(N—ethyl-N—$\beta$-hydroxyethylamino)-2-methylaniline sulfate | 4.5 g |
| Water | to 1 liter |
| Bleaching Solution | |
| Ammonium bromide | 160.0 g |
| Ammonia water (28%) | 25.0 ml |
| Sodium iron ethylenediaminetetraacetate | 130.0 g |
| Glacial acetic acid | 14 ml |
| Water | to 1 liter |
| Fixing Solution | |
| Sodium tetrapolyphosphate | 2.0 g |
| Sodium nitrite | 4.0 g |
| Ammonium thiosulfate (70%) | 175.0 ml |
| Sodium bisulfite | 4.6 g |
| Water | to 1 liter |
| Stabilizing Solution | |
| Formalin | 3.0 ml |
| Water | to 1 liter |

The density of each processed sample was measured using red light. The results are shown in Table 1.

TABLE 1

| Sample | Coupler | Relative Sensitivity* | Maximum Density |
| --- | --- | --- | --- |
| 201 | EX-1 (Comparative) | 100 | 2.17 |
| 202 | C-4 (Comparative) | 89 | 2.15 |
| 203 | C-5 (Comparative) | 95 | 2.19 |
| 204 | C-6 (Comparative) | 93 | 2.20 |
| 205 | (1) (Invention) | 115 | 2.32 |
| 206 | (2) (Invention) | 110 | 2.25 |
| 207 | (3) (Invention) | 112 | 2.23 |

TABLE 1-continued

| Sample | Coupler | Relative Sensitivity* | Maximum Density |
| --- | --- | --- | --- |
| 208 | (6) (Invention) | 108 | 2.22 |

*The inverse number of the exposure giving a density of fogging + 0.2, expressed as the relative sensitivity (relative to the value of sample 201 being taken as 100).

It can be seen from Table 1 that the couplers of this invention are high in both sensitivity and developed color density and are excellent in color developing properties.

EXAMPLE 2

In order to examine the reduction in the cyan color density by an exhausted bleaching solution, samples 201, 202, 205, 206, 207, and 208 obtained in Example 1 were exposed to light for sensitometry, then developed and processed in the same manner as in Example 1, except that, of the developing and processing steps of Example 1, only the bleaching solution was replaced by that of the following composition. The color density was measured using red light, and the results are shown in Table 2.

| Bleaching Solution | |
| --- | --- |
| Ammonium bromide | 160.0 g |
| Ammonia water (28%) | 25.0 ml |
| Sodium iron ethylenediaminetetraacetate | 130.0 g |
| Glacial acetic acid | 14 ml |
| Sodium hydrosulfite | 4.0 g |
| Water | to 1 liter |

TABLE 2

| Sample | Coupler | Maximum Density | Residual Color Image Rate* |
| --- | --- | --- | --- |
| 201 | EX-1 (Comparative) | 1.82 | 84% |
| 202 | C-4 (Comparative) | 1.76 | 82% |
| 205 | (1) (Invention) | 2.27 | 98% |
| 206 | (2) (Invention) | 2.25 | 100% |
| 207 | (3) (Invention) | 2.21 | 99% |
| 208 | (6) (Invention) | 2.13 | 96% |

*Residual Color Image Rate = Maximum Density (Ex. 2)/Maximum Density (EX. 1) × 100

It can be seen from Table 2 that the samples 201 and 202 utilizing the naphthol type cyan couplers caused great reduction in the color density when processed with the model bleaching solution for the exhausted solution, whereas with the samples utilizing the cyan couplers of this invention, there was almost no reduction in the color density.

EXAMPLE 3

The film samples 201, 202, 205 and 207 obtained in Example 1 were exposed to light for sensitometry, then developed and processed in the same manner as in Example 1. Using the obtained processed samples respectively, a test on fastness of color images was conducted under the following three conditions: (i) placed in a dark place at 100° C. for 14 days, (ii) placed in a dark place at 60° C. and 70% RH for 4 weeks, and (iii) exposed to a xenon tester (100,000 lux) for 7 days. The results are shown in Table 3.

TABLE 3

| | | Residual Color Image Rate (%) | | |
| --- | --- | --- | --- | --- |
| Sample | Coupler | 100° C. 14 days | 60° C. 70% RH 4 weeks | Xenon light 100,000 lux 7 days |
| 201 | EX-1 (Comparative) | 58 | 93 | 97 |
| 202 | C-1 (Comparative) | 61 | 94 | 97 |
| 205 | (1) (Invention) | 95 | 99 | 98 |
| 206 | (3) (Invention) | 97 | 99 | 97 |

It can be seen from Table 3 that the color image formed with the couplers of this invention are excellent in fastness.

EXAMPLE 4

A multi-layered color photographic material sample was prepared, which was composed of the respective layers of the following compositions on a cellulose acetate film base, and was designated as sample 301.

| First Layer: Antihalation Coating | |
| --- | --- |
| Gelatin layer containing black colloidal silver | |
| Second Layer: Intermediate Layer | |
| Gelatin layer containing an emulsified dispersion of 2,5-di-tert-octylhydroquinone | |
| Third Layer: First Red-Sensitive Emulsion Layer: | |
| Silver iodobromide emulsion (silver iodide: 5 mole %) | |
| Silver concentration | 1.6 g/m$^2$ |
| Sensitizing Dye I (per mole of silver) | 4.5 × 10$^{-4}$ mole |
| Sensitizing Dye II (per mole of silver) | 1.5 × 10$^{-4}$ mole |
| Coupler EX-4 (per mole of silver) | 0.015 mole |
| Coupler EX-5 (per mole of silver) | 0.015 mole |
| Coupler EX-2 (per mole of silver) | 0.003 mole |
| Coupler EX-3 (per mole of silver) | 0.0008 mole |
| Fourth Layer: Second Red-Sensitive Emulsion Layer | |
| Silver iodobromide emulsion (silver iodide: 10 mole %) | |
| Silver concentration | 1.4 g/m$^2$ |
| Sensitizing Dye I (per mole of silver) | 3.0 × 10$^{-4}$ mole |
| Sensitizing Dye II (per mole of silver) | 1.0 × 10$^{-4}$ mole |
| Coupler EX-6 (per mole of silver) | 0.005 mole |
| Coupler C-3 (per mole of silver) | 0.017 mole |
| Coupler EX-2 (per mole of silver) | 0.0016 mole |
| Fifth Layer: Intermediate Layer | |
| Same as the second layer | |
| Sixth Layer: First Green-Sensitive Emulsion Layer | |
| Silver iodobromide emulsion (silver iodide: 4 mole %) | |
| Silver concentration | 1.2 g/m$^2$ |
| Sensitizing Dye III (per mole of silver) | 5.0 × 10$^{-4}$ mole |
| Sensitizing Dye IV (per mole of silver) | 2.0 × 10$^{-4}$ mole |
| Coupler EX-7 (per mole of silver) | 0.05 mole |
| Coupler EX-8 (per mole of silver) | 0.008 mole |
| Coupler EX-9 (per mole of silver) | 0.0018 mole |
| Seventh Layer: Second Green-Sensitive Emulsion Layer | |
| Silver iodobromide emulsion (silver iodide: 8 mole %) | |
| Silver concentration | 1.3 g/m$^2$ |
| Sensitizing Dye III (per mole of silver) | 3.0 × 10$^{-4}$ mole |
| Sensitizing Dye IV (per mole of silver) | 1.2 × 10$^{-4}$ mole |
| Coupler EX-10 (per mole of silver) | 0.017 mole |
| Coupler EX-11 (per mole of silver) | 0.003 mole |
| Eighth Layer: Yellow Filter Layer | |
| Gelatin layer containing an emulsified dispersion of yellow colloidal silver and 2,5-di-tert-octylhydroquinone in a gelatin aqueous solution. | |
| Ninth Layer: First Blue-Sensitive Emulsion Layer | |
| Silver iodobromide (silver iodide: 6 mole %) | |
| Silver concentration | 0.7 g/m$^2$ |
| Coupler EX-12 (per mole of silver) | 0.25 mole |
| Coupler EX-13 (per mole of silver) | 0.015 mole |
| Tenth Layer: Second Blue-Sensitive Emulsion Layer | |
| Silver iodobromide emulsion (silver iodide: 6 mole %) | |
| Silver concentration | 0.6 g/m$^2$ |
| Coupler EX-12 (per mole of silver) | 0.06 mole |
| Eleventh Layer: First Protective Layer | |
| Silver iodobromide (silver iodide: 1 mole %, ave. grain diameter: 0.07 μ) | |
| Silver dosage | 0.5 g/m$^2$ |
| Gelatin layer containing an emulsified dispersion of a UV absorber UV-1 | |
| Twelfth Layer: | |
| Gelatin layer containing polymethyl methacrylate particles (diameter: 1.5 μ) | |

In addition to the above compositions, the respective layers further contained a gelatin hardener, i.e., 1,3-divinylsulfonyl-2-propanol, a high boiling organic solvent for emulsifying and dispersing the couplers, etc. (e.g., tricresyl phosphate, dibutyl phthalate, etc.) and a surfactant. The sample thus prepared was designated as Sample 301.

| Compounds Used For the Preparation of the Sample: | |
| --- | --- |
| Sensitizing dye III: | Anhydro-9-ethyl-5,5'-dichloro-3,3'-di-(γ-sulfopropyl)oxacarbocyanine sodium salt |
| Sensitizing dye IV: | Anhydro-5,6,5',6'-tetrachloro-1,1'-diethyl-3,3'-{β-[β-(γ-sulfopropoxy)ethoxy]ethylimidazolocarbocyanine}hydroxide sodium |

-continued
Compounds Used For the Preparation of the Sample:
EX-4
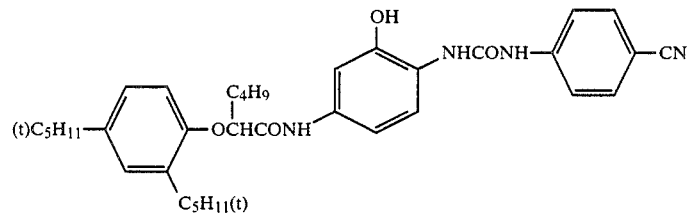
EX-5
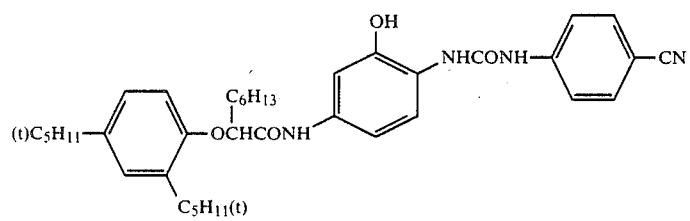
EX-6
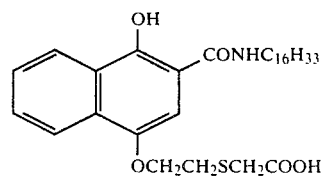
EX-7
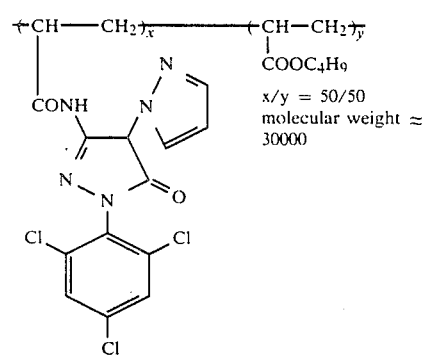
x/y = 50/50
molecular weight ≈ 30000
EX-8
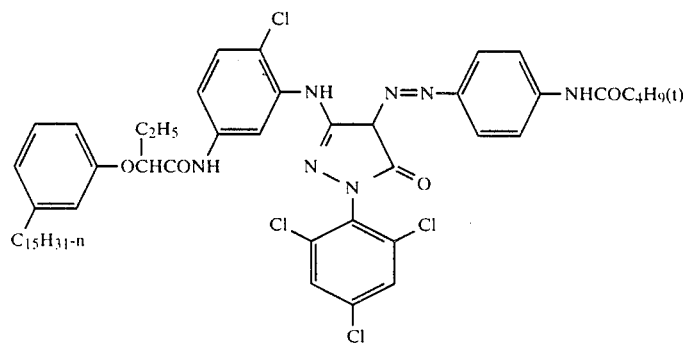

-continued
Compounds Used For the Preparation of the Sample:
EX-9
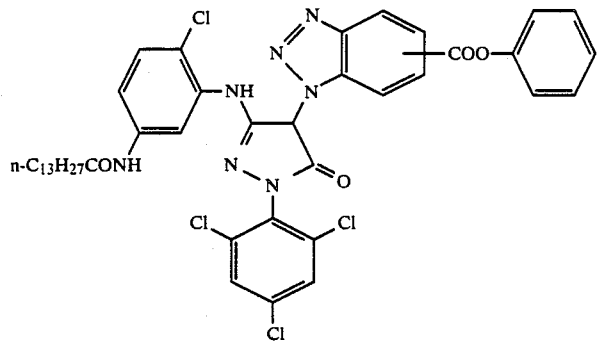
EX-10
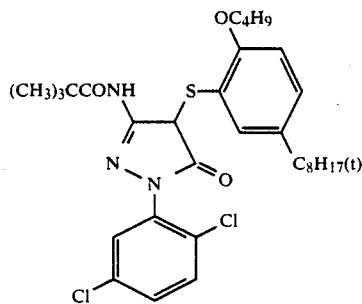
EX-11
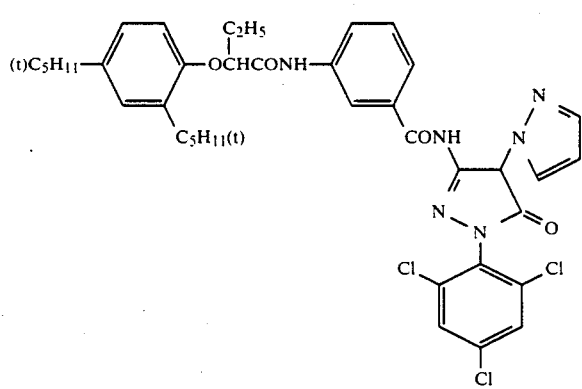
EX-12
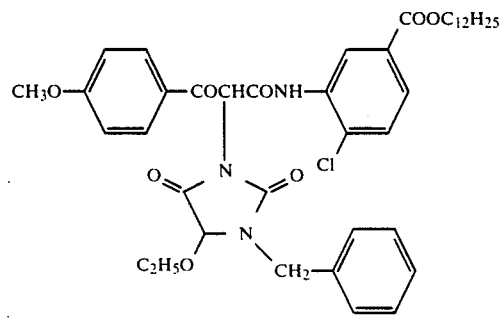

-continued

Compounds Used For the Preparation of the Sample:

EX-13

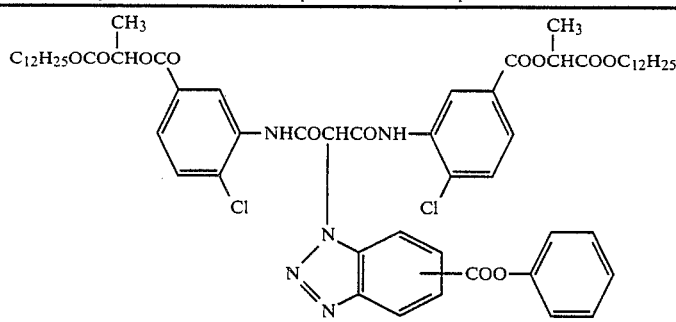

UV-1

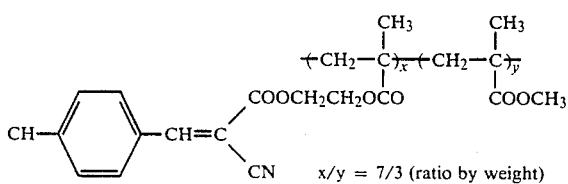

x/y = 7/3 (ratio by weight)

Samples were prepared in a manner similar to the above except that the coupler C-3 in the fourth layer of the sample 301 was replaced by the same molar amounts of the couplers (1) and (3) respectively, and were designated as samples 302 and 303. Furthermore, using various high boiling organic solvents for dispersing the couplers, samples 304, 305, 306 and 307 were prepared as shown in Table 4. The samples 301–307 obtained were exposed to light for sensitometry, then developed and processed in a manner similar to that in Example 2. The density was measured using red light, and the results are shown in Table 4.

TABLE 4

| Sample | Coupler | High Boiling Organic Solvent* | Sensitivity** | Gamma |
|---|---|---|---|---|
| 301 | C-3 (Comparative) | S-1, S-2 | 100 | 0.75 |
| 302 | (1) (Invention) | S-1, S-2 | 107 | 0.83 |
| 303 | (3) (Invention) | S-1, S-2 | 105 | 0.81 |
| 304 | (3) (Invention) | S-1, S-3 | 105 | 0.80 |
| 305 | (3) (Invention) | S-2, S-4 | 107 | 0.84 |
| 306 | (3) (Invention) | S-3, S-4 | 105 | 0.81 |
| 307 | (3) (Invention) | S-1, S-4 | 102 | 0.79 |

*S-1: Tricresyl phosphate
S-2: Dibutyl phthalate
S-3: Dioctyl phthalate
S-4: Trioctyl phosphate
In the samples 301–307, the two kinds of the high boiling organic solvents were added in amounts of 0.5 ml respectively per g of the cyan coupler.
**The inverse number of the exposure giving a density of fogging + 0.3, expressed as the relative sensitivity (relative to the value of sample 301 being taken as 100).

It can be seen from Table 4 that the couplers of this invention are excellent in color developing properties. Further, it is also found that the couplers of this invention have excellent color developing properties and good emulsion stability even when using different high boiling organic solvents.

While the invention has been described in detail and with reference to specific embodiments thereof, it will be apparent to one skilled in the art that various changes and modifications can be made therein without departing from the spirit and scope thereof.

What is claimed is:

1. A silver halide color photographic material comprising as a cyan-dye-forming coupler a compound represented by formula (I)

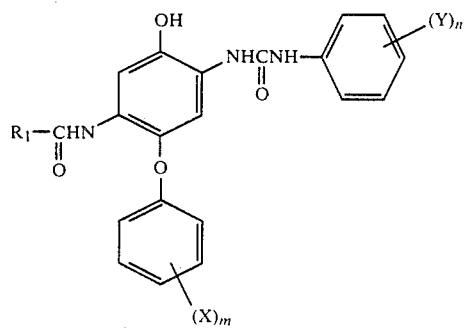

wherein $R_1$ represents a ballast group represented by formula (II):

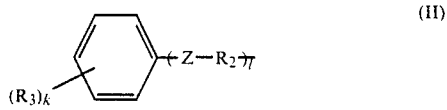

wherein Z represents an oxygen atom, a sulfur atom, —SO—, or —SO$_2$; k is 2 to 4, and l represents 0 or 1, the $R_3$ are the same or different; $R_2$ represents a straight-chain or branched-chain alkylene group having from 1 to 24 carbon atoms; and $R_3$ represents a halogen atom, an alkyl group, an aryl group, a heterocyclic group, an alkoxy group, an aryloxy group, a hydroxyl group, an acyloxy group, a carboxyl group, an alkoxycarbonyl group, an aryloxycarbonyl group, an alkylthio group, an acyl group, a carbonamido group, a sulfonamido group, a carbamoyl group, or a sulfamoyl group; X represents a substituted or unsubstituted alkyl group or an unsubstituted alkoxy group Y represents a group selected from a halogen atom, a cyano group, a trifluoromethyl group, an arylsulfonyl group, an alkylsulfonyl group, a sulfonamido group, a sulfamoyl group, a carbamoyl group, or an alkoxycarbonyl group; m and n each represents an integer of 1 to 5, and when m or n is more than 1, the X or Y, respectively, are the same or different; with the proviso that the total number of carbon atoms in the substituent $(X)_m$ is 4 to 32.

2. A silver halide color photographic material as in claim 1, wherein the compound represented by formula (I) is present in an amount of from $1 \times 10^{-3}$ mole to $7 \times 10^{-1}$ mole per mole of silver in a silver halide emulsion layer constituting a photosensitive layer of said silver halide color photographic material.

3. A silver halide color photographic material as in claim 1, wherein the compound represented by formula (I) is present in an amount of from $1 \times 10^{-2}$ mole to $5 \times 10^{-1}$ mole per mole of silver in a silver halide emulsion layer constituting a photosensitive layer of said silver halide color photographic material.

4. A silver halide color photographic material as in claim 1, wherein X represents said substituted or unsubstituted alkyl group.

5. A silver halide color photographic material as in claim 1, wherein the total number of carbon atoms in the substituent $(X)_m$ is from 8 to 32.

6. A silver halide color photographic material as in claim 1, wherein X is said unsubstituted alkoxy group.

7. A silver halide color photographic material as in claim 1, wherein X represents a member selected from the group consisting of: $(t)C_5H_{11}-$; $(t)C_4H_9-$; $(t)C_8H_{17}-$; $n-C_{15}H_{31}-$; $n-C_8H_{17}O-$; $n-C_{10}H_{21}-$; and $(t)C_{10}H_{21}-$.

8. A silver halide color photographic material as in claim 1, wherein $R_3$ in formula (II) represents a halogen atom, an alkyl group or an alkoxy group, and Z in formula (II) represents an oxygen atom.

9. A silver halide color photographic material according to claim 1, wherein Y represents a group selected from a cyano group, a trifluoromethyl group, an arylsulfonyl group, an alkylsulfonyl group, a sulfonamido group, a sulfamoyl group, a carbamoyl group, or an alkoxycarbonyl group.

10. The silver halide color photographic material according to claim 1, wherein X is an unsubstituted alkyl group or an unsubstituted alkoxy group.

11. The silver halide color photographic material according to claim 4, wherein X is located in a position para to the oxygen atom which is attached to the same benzene ring as X.

* * * * *

UNITED STATES PATENT AND TRADEMARK OFFICE
CERTIFICATE OF CORRECTION

PATENT NO. : 4,910,128

DATED : March 20, 1990

INVENTOR(S) : TAKAYOSHI KAMIO; KATSUYOSHI YAMAKAWA; HIDETOSHI KOBAYASHI; and ISAMU ITOH Page 1 of 4

It is certified that error appears in the above-indentified patent and that said Letters Patent is hereby corrected as shown below:

At Columns 5 and 6, lines 30 to 67 delete Compound Examples (1) to (6) in their entirety and insert therefor

| | | | | | |
|---|---|---|---|---|---|
| -- (1) | (t)C$_5$H$_{11}$—⟨phenyl, C$_5$H$_{11}$(t)⟩—OCH(C$_4$H$_9$)— | (t)C$_5$H$_{11}$— (2, 4)* | NC— (4)** | 2 | 1 |
| (2) | (t)C$_5$H$_{11}$—⟨phenyl, C$_5$H$_{11}$(t)⟩—OCH(C$_6$H$_{13}$)— | (t)C$_4$H$_9$— (4) | NC— (4) | 1 | 1 |
| (3) | (t)C$_5$H$_{11}$—⟨phenyl, C$_5$H$_{11}$(t)⟩—OCH(C$_4$H$_9$)— | (t)C$_8$H$_{17}$— (4) | NC— (4) | 1 | 1 |
| (4) | (t)C$_5$H$_{11}$—⟨phenyl, C$_5$H$_{11}$(t)⟩—OCH(C$_2$H$_5$)— | (t)C$_8$H$_{17}$— (2, 4) | NC— (4) | 2 | 1 |
| (5) | (t)C$_8$H$_{17}$—⟨phenyl, C$_8$H$_{17}$(t)⟩—OCH(C$_6$H$_{13}$)— | (t)C$_8$H$_{17}$— (4) | Cl— (3, 4) | 1 | 2 |
| (6) | (t)C$_5$H$_{11}$—⟨phenyl, C$_5$H$_{11}$(t)⟩—OCH(C$_2$H$_5$)— | (t)C$_8$H$_{17}$— (4) | C$_4$H$_9$SO$_2$— (4) | 1 | 1 -- |

UNITED STATES PATENT AND TRADEMARK OFFICE
CERTIFICATE OF CORRECTION

PATENT NO. : 4,910,128   Page 2 of 4

DATED : March 20, 1990

INVENTOR(S) : TAKAYOSHI KAMIO; KATSUYOSHI YAMAKAWA; HIDETOSHI KOBAYASHI; and ISAMU ITOH It is certified that error appears in the above-indentified patent and that said Letters Patent is hereby corrected as shown below:

At Columns 7 and 8, lines 30 to 68 delete Compound Examples (7) to (14) in their entirety and insert therefor -- (7)
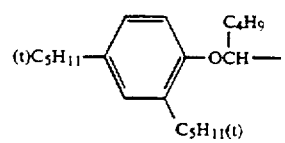
(t)$C_5H_{11}-$  CH$_3$SO$_2-$   1  1
(4)              (4)

(8)
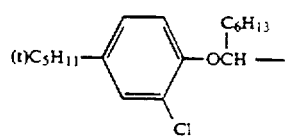
n-$C_{15}H_{31}-$  NC$-$   1  1
(3)                (4)

(9)
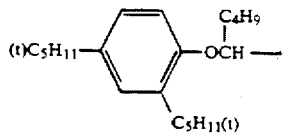
n-$C_8H_{17}O-$   CH$_3$SO$_2$NH$-$   1  1
(4)               (3)

(10)
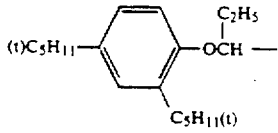
CH$_3-$, n-$C_{10}H_{21}-$   $-SO_2N\begin{smallmatrix}C_2H_5\\C_2H_5\end{smallmatrix}$   2  1
(4)     (2)

(11)
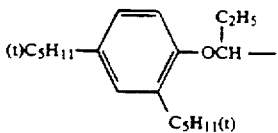
(t)$C_8H_{17}-$, CH$_3$O$-$   CF$_3-$   2  1
(4)              (2)          (4)

UNITED STATES PATENT AND TRADEMARK OFFICE
CERTIFICATE OF CORRECTION

PATENT NO. : 4,910,128
DATED : March 20, 1990
INVENTOR(S) : TAKAYOSHI KAMIO; KATSUYOSHI YAMAKAWA; HIDETOSHI KOBAYASHI; and ISAMU ITOH It is certified that error appears in the above-indentified patent and that said Letters Patent is hereby corrected as shown below:

(12) 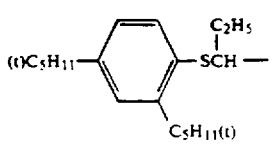  (t)C₈H₁₇— (4)   C₄H₉SO₂— (4)   1   1

(13) 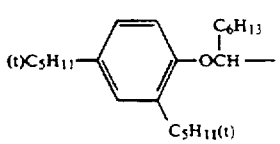  (t)C₈H₁₇—, CH₃CONH— (4)   (2)   NC— (4)   2   1

(14) 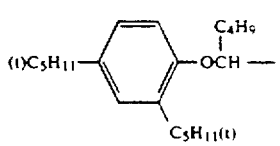  (t)C₁₀H₂₁—, Cl— (4)   (2)   NC— (4)   2   1   — —

At Column 9 and 10, lines 30 to 55 delete Compound Examples (15) to (20) in their entirety and insert therefor — — (15) 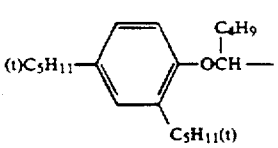   (t)C₈H₁₇— (4)   Cl—, NC— (2)   (4)   1   2

(16) 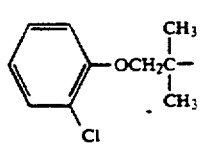   (t)C₁₀H₂₁— (4)   NC— (4)   1   1

UNITED STATES PATENT AND TRADEMARK OFFICE
CERTIFICATE OF CORRECTION

PATENT NO. : 4,910,128
DATED : March 20, 1990
INVENTOR(S) : TAKAYOSHI KAMIO; KATSUYOSHI YAMAKAWA; HIDETOSHI KOBAYASHI; and ISAMU ITOH It is certified that error appears in the above-indentified patent and that said Letters Patent is hereby corrected as shown below:

Signed and Sealed this

Second Day of August, 1994

Attest:

BRUCE LEHMAN

Attesting Officer     Commissioner of Patents and Trademarks